United States Patent [19]
Radomski et al.

[11] Patent Number: 5,849,491
[45] Date of Patent: Dec. 15, 1998

[54] METHOD FOR ISOLATING XYLANASE GENE SEQUENCES FROM SOIL DNA, COMPOSITIONS USEFUL IN SUCH METHOD AND COMPOSITIONS OBTAINED THEREBY

[75] Inventors: Christopher C. A. Radomski, Abbotsford, Canada; Kah Tong Seow, Singapore, Singapore; R. Antony J. Warren, Vanouver, Canada; Wai Ho Yap, Singapore, Singapore

[73] Assignee: Terragen Diversity Inc., Vancouver, Canada

[21] Appl. No.: 716,942

[22] Filed: Sep. 20, 1996

Related U.S. Application Data

[60] Provisional application No. 60/004,157, Sep. 22, 1995.
[51] Int. Cl.$^6$ .............................. C12Q 1/68; C12P 19/34
[52] U.S. Cl. .............................. 435/6; 435/91.2; 935/77; 935/78
[58] Field of Search .............................. 435/6, 91.2, 91.1, 435/5; 536/23.1, 24.3–24.33

[56] References Cited

U.S. PATENT DOCUMENTS 5,610,048   3/1997   Schulein et al. ..................... 435/209

FOREIGN PATENT DOCUMENTS

| 0517418 | 12/1992 | European Pat. Off. . |
| 6277061 | 10/1994 | Japan . |
| 9118974 | 12/1991 | WIPO . |
| 9514770 | 6/1995 | WIPO . |
| 9518219 | 7/1995 | WIPO . |
| 9534662 | 12/1995 | WIPO . |

OTHER PUBLICATIONS

Porteous et al. Current Microbiology 29: 301–307, 1994.
Tebbe et al. Applied and Environmental Microbiology 59: 2657–2665, 1993.
Steffan et al. Ann Rev, Microbiology 45: 137–61, 1991.
Smalla et al. J. of Applied Bscteriology 74: 78–85, 1993.
Porteous and Armstrong Current Microbiology 27: 115–118, 1993.
Porteous and ASrmstron Current Microbiology 22: 345–348, 1991.
Johnston and Aust Applied and Environmental Microbiology 60: 2350–2354, 1994.
Saddler, J.N., *Bioconversion of Forest and Agricultural Plant Residues*, CAB Int'l, Wallingford, England, pp. 1–11 (1993).
Wick, C.B., "Enzymology Advances Offer Economical and Environmentally Safe ways to Make Paper", *Genetic Engineering News* 14: 1 (1994).
McCubbin, N., "A Bleaching Revolution is in Progress", *Pulp & Paper Canada* 94: 12–16 (1994).
Tiedje, J.M., "Microbial Diversity: Of Value to Whom?", *ASM News* 60: 524–525 (1994).
Bergquist et al., "Hemicellulolytic Enzymes From Extremely Thermophilic Bacteria–Application of Molecular Genetics to Pulp Bleaching", poster presented at Society for Industrial Microbiology Meeting, Montreal, Canada, Jun. 1994.
Barns et al., "Remarkable archael diversity detected in a Yellowstone National Park hot spring environment", *Proc. Nat'l Acad. Sci.* (*USA*) 91: 1609–1613 (1994).
Holben et al., "DNA Probe Method for the Detection of Specific Microorganisms in the Soil Bacterial Community", *Appl. Environ. Microbiol.* 54: 703–711 (1988).
Patil et al., "PCR Amplification of an *Escherichia coli* gene using mixed primers contianing deoxyadensine at ambiguous positions in degenerate amino acid codons" *Nucl. Acids Res.* 18: 3080 (1990).
Don et al., "Touchdown PCR to circumvent spurious priming during gene amplification", *Nucl. Acids Res.* 19: 4008 (1991).
Roux, K.H., "Using Mismatched Primer–Template pairs in Touchdown PCR", *BioTechniques* 16: 812–814 (1994).
Matsumura et al, "DNA Shuffling Brightens Prospects for GFP" Nature Biotechnology 14:314 (1996).
Crameri et al., "Improved Green Fluorescent Protein by Molceular Evolution Using DNA Shuflfing", *Nature Biotechnology* 14: 315–319 (1996).
Munro et al., "A gene encoding a thermophilic alkaline serine proteinase from Thermus sp. strain Rt41A and its expression in *Escherichia coli*", *Microbiology* 141: 1731–1738 (1995).

*Primary Examiner*—Lisa B. Arthur
*Attorney, Agent, or Firm*—Oppedahl & Larson

[57] ABSTRACT

Xylanase DNA is recovered from soil by PCR amplification using degenerate primers. Because of the complexity of the soil samples, it is likely that the recovered product will include more than one species of polynucleotide. These recovered copies may be cloned into a host organism to produce additional copies of each individual species prior to characterization by sequencing. Recovered DNA which is found to vary from known xylanases can be used in several ways to facilitate production of novel xylanases for industrial application. First, the recovered DNA, or probes corresponding to portions thereof, can be used as a probe to screen DNA libraries and recover intact xylanase genes including the unique regions of the recovered DNA. Second, the recovered DNA or polynucleotides corresponding to portions thereof, can be inserted into a known xylanase gene to produce a recombinant xylanase gene with the sequence variations of the recovered DNA.

7 Claims, 2 Drawing Sheets

1. Forward primer from Bergquist et al.
2. Forward primer from the present invention.
3. Reverse primer from Bergquist et al.
4. Reverse primer from the present invention.

Fig. 2

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: yes ( v ) FRAGMENT TYPE: internal ( v i ) ORIGINAL SOURCE:
        ( A ) ORGANISM:

( i x ) FEATURE:
        ( A ) NAME/KEY: degenerate primer for amplification of xylanase
            fragments from soil ( x i ) SEQUENCE DESCRIPTION: SEQ ID NO:1:

CGSGGSCACA CSNTSNTSTG G        2 1

( 2 ) INFORMATION FOR SEQ ID NO:2:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM:

( i x ) FEATURE:
        ( A ) NAME/KEY: degenerate primer for amplification of xylanase
            fragments from soil ( x i ) SEQUENCE DESCRIPTION: SEQ ID NO:2:

GTTGTAGTCG TTGWNGNASA        2 0

( 2 ) INFORMATION FOR SEQ ID NO:3:

( i ) SEQUENCE CHARACTERISTICS:
    ( A ) LENGTH: 269
    ( B ) TYPE: nucleic acid
    ( C ) STRANDEDNESS: double
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM:

( i x ) FEATURE:
    ( A ) NAME/KEY: fragment of xylanase gene from degenerate primer
        amplification of soil DNA ( x i ) SEQUENCE DESCRIPTION: SEQ ID NO:3:

```
GGGGCCACAC GGTCGTGTGG GCGGTGGACG ACTTTGTGCA GTCATGGATC        50
AAAAACCTTT CCAACGGGGA CCTGCGGATC CATTTGACCA ACCGCATCGA       100
AAGCGTAGTC ATTCATTTCA CGGGCACCTT CATGCATCGG GATGTGAACA       150
ACGAAATGTT GCACGGCAAT TACTACGGCA ACCGCCTCGG CGATTCCATC       200
AACTCCTGGA TGTTCAAACA CGCCCGCTTG CAGGACAGCA ACGTCGTGCT       250
CTCCCTCAAC GACTACAAC                                          269
```

( 2 ) INFORMATION FOR SEQ ID NO:4:

( i ) SEQUENCE CHARACTERISTICS:
        ( A ) LENGTH: 288
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM:

( i x ) FEATURE:
        ( A ) NAME/KEY: fragment of xylanase gene from degenerate primer
            amplification of soil DNA ( x i ) SEQUENCE DESCRIPTION: SEQ ID NO:4:

```
CGCGGGCACA CCGTCGTGTG GCACAACCAG CTTCCCGGGT GGGTGACGGC        50
GACGGCCGCG AGCAGCGACG AGCAGGCCGC GGTGCTGCAG GCGCACGTCA       100
CTCAGGAGGT CGACCACTTC CGCGGCCACA TCTACGCGTG GGACGTCGTC       150
AACGAGCCGT TCAACGATGA CGGCACCTGG CGCGACACCA TCTGGTACCG       200
CCCCATGGGT CCGGACTACA TCGCGCAGGC CTTCCGCTGG GTCCGCGCGG       250
CGGACCTAGA TGCCCGGCTG TCCCACAACG ACTACAAC                    288
```

( 2 ) INFORMATION FOR SEQ ID NO:5:

( i ) SEQUENCE CHARACTERISTICS:
        ( A ) LENGTH: 288
        ( B ) TYPE: nucleic acid
        ( C ) STRANDEDNESS: double (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
    (A) ORGANISM:

(ix) FEATURE:
    (A) NAME/KEY: fragment of xylanase gene from degenerate primer amplification of soil DNA (xi) SEQUENCE DESCRIPTION: SEQ ID NO:5:

| | | | | | |
|---|---|---|---|---|---|
| CGGGGGCACA | CGGTGGTGTG | GCACAACCAG | CTTCCCGGGT | GGGTGACGGC | 50 |
| GACGGCCGCG | AGCAGCGACG | AGCAGGCCGC | GGTGCTGCAG | GCGCACGTCA | 100 |
| CTCAGGAGGT | CGACCACTTC | CGCGGCCACA | TCTACGCGTG | GGACGTCGTC | 150 |
| AACGAGCCGT | TCAACGATGA | CGGCACCTGG | CGCGACACCA | TCTGGTACCG | 200 |
| CGCCATGGGT | CCGGACTACA | TCGCGCAGGC | CTTCCGCTGG | GCTCGCGCGG | 250 |
| CGGACCTAGA | TGCCCGGCTG | TCCCTCAACG | ACTACAAC | | 288 |

(2) INFORMATION FOR SEQ ID NO:6:

(i) SEQUENCE CHARACTERISTICS:
        (A) LENGTH: 288
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
    (A) ORGANISM:

(ix) FEATURE:
    (A) NAME/KEY: fragment of xylanase gene from degenerate primer amplification of soil DNA (xi) SEQUENCE DESCRIPTION: SEQ ID NO:6:

| | | | | | |
|---|---|---|---|---|---|
| CGTGGGCACA | CCGTCGTGTG | GCACAACCAG | CTGCCCGGCT | GGGTCACCAC | 50 |
| CGGTGCCTTC | AGCAGCGACG | AGCTCGCCGT | CATCCTGCAG | CAGCACATCA | 100 |
| CCGAGAAGGT | CGGACACTTC | GCCGGGCACA | TCTCCGTGTG | GGACGTGGTC | 150 |
| ATCGAGCCGC | TCAACGACGA | TGGCACCTGG | CGCGACACCA | TCTGGTACCG | 200 |
| CGCTCTGGGT | CCGGGTTACG | TCACGCAGGC | GTTGCGCTGG | GCGCACGCGG | 250 |
| CTGACCCCGG | CGCCAGGCTG | TCCCTCAACG | ACTACAAC | | 288 |

(2) INFORMATION FOR SEQ ID NO:7:

(i) SEQUENCE CHARACTERISTICS:
        (A) LENGTH: 269
        (B) TYPE: nucleic acid
        (C) STRANDEDNESS: DOUBLE
        (D) TOPOLOGY: linear (ii) MOLECULE TYPE: genomic DNA (  i i i  ) HYPOTHETICAL: no (  i v  ) ANTI-SENSE: no (  v  ) FRAGMENT TYPE: internal (  v i  ) ORIGINAL SOURCE:
    ( A ) ORGANISM:

(  i x  ) FEATURE:
    ( A ) NAME/KEY: fragment of xylanase gene from degenerate primer
        amplification of soil DNA (  x i  ) SEQUENCE DESCRIPTION: SEQ ID NO:7:

| | | | | | |
|---|---|---|---|---|---|
| GGCACAACCA | GTTGCCAGCC | TGGCTCACAA | GCGGTGCATT | CAGCAGCGCC | 5 0 |
| GAGCTGGCCA | CCATCCTGGA | GCAGCACGTC | ACCCAGGAAG | CGGACCATTT | 1 0 0 |
| CCGCGGGCAC | ATCTACGCCT | GGGACATCGT | CAACGAGCCG | TTCAACGACG | 1 5 0 |
| ATGGCACCTG | GCGTGACAGC | CTCTGGTACC | GCGCGCTGGG | CGCCGGCTAC | 2 0 0 |
| GTCGCCCAGG | CGTTGCGCTG | GGCCCGCGCG | GCCGATCCGT | CTGCCCGGTT | 2 5 0 |
| CTCCCTCAAC | GACTACAAC | | | | 2 6 9 |

( 2 ) INFORMATION FOR SEQ ID NO:8:

(  i  ) SEQUENCE CHARACTERISTICS:
    ( A ) LENGTH: 282
    ( B ) TYPE: nucleic acid
    ( C ) STRANDEDNESS: DOUBLE
    ( D ) TOPOLOGY: linear (  i i  ) MOLECULE TYPE: genomic DNA (  i i i  ) HYPOTHETICAL: no (  i v  ) ANTI-SENSE: no (  v  ) FRAGMENT TYPE: internal (  v i  ) ORIGINAL SOURCE:
    ( A ) ORGANISM:

(  i x  ) FEATURE:
    ( A ) NAME/KEY: fragment of xylanase gene from degenerate primer
        amplification of soil DNA (  x i  ) SEQUENCE DESCRIPTION: SEQ ID NO:8:

| | | | | | |
|---|---|---|---|---|---|
| CGCGGGCACA | CCGTCGTCTG | GCACTCGCAA | CTGCCGTCGT | GGGTCAGTAA | 5 0 |
| TCTTCCGACC | AACCAGGTGC | AGTCGGTGAT | GGAAGCCCAC | ATCACGACCG | 1 0 0 |
| AGGCCACCCA | CTACAAGGGG | AAGGTCTACG | CCTGGGACGT | CGTCAATGAA | 1 5 0 |
| CCGTCCAACG | ACGACGGTAC | GCTGCGCCAG | GAGGTTTTCT | ATCGTGCCAT | 2 0 0 |
| GGGCACCGGC | TACATCGCCG | ACGCGATCCG | TACCGCCCAC | ACCGCCGACC | 2 5 0 |
| CCACCGCCAA | GCTCTCCCAC | AACGACTACA | AC | | 2 8 2 |

( 2 ) INFORMATION FOR SEQ ID NO:9:

(  i  ) SEQUENCE CHARACTERISTICS:
    ( A ) LENGTH: 282
    ( B ) TYPE: nucleic acid
    ( C ) STRANDEDNESS: DOUBLE
    ( D ) TOPOLOGY: linear (  i i  ) MOLECULE TYPE: genomic DNA (  i i i  ) HYPOTHETICAL: no (  i v  ) ANTI-SENSE: no -continued ( v ) FRAGMENT TYPE: internal ( v i ) ORIGINAL SOURCE:
    ( A ) ORGANISM:

( i x ) FEATURE:
    ( A ) NAME/KEY: fragment of xylanase gene from degenerate primer
        amplification of soil DNA ( x i ) SEQUENCE DESCRIPTION: SEQ ID NO:9:

| | | | | | |
|---|---|---|---|---|---|
| CGGGGGCACA | CGGTCGTCTG | GCACTCGCAA | CTGCCGTCGT | GGGTCAGTAA | 50 |
| TCTCCCGACC | AACCAGGTGC | AGTCGGTGAT | GGAAGCCCAC | ATCACGACCG | 100 |
| AGGCCACCCA | CTACAAGGGG | AAGGTCTACG | CCTGAGACGT | CGTCAATGAA | 150 |
| CCGTTCAACG | ACGACGGTAC | GCTGCGCCAG | GACGTTTTCT | ATCGTGCCAT | 200 |
| GGGCACCGGC | TACATCGCCG | ACGCGATCCG | TACCGCCCAC | ACCGCCGACC | 250 |
| CCACCGCCAA | GCTCTCCCTC | AACGACTACA | AC | | 282 |

( 2 ) INFORMATION FOR SEQ ID NO:10:

( i ) SEQUENCE CHARACTERISTICS:
        ( A ) LENGTH: 288
        ( B ) TYPE: nucleic acid
        ( C ) STRANDEDNESS: DOUBLE
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM:

( i x ) FEATURE:
        ( A ) NAME/KEY: fragment of xylanase gene from degenerate primer
            amplification of soil DNA ( x i ) SEQUENCE DESCRIPTION: SEQ ID NO:10:

| | | | | | |
|---|---|---|---|---|---|
| CGGGGGCACA | CCGTCGTGTG | GCACTCGCAG | CTCTCCACCT | GGCTGACGTC | 50 |
| GGGCACGTGG | ACCGCCGCGC | AGGCGACGAC | GCTGATGACG | GACCACATCG | 100 |
| CCAACGTCGT | CGGCCACTAC | AAGGGGCAGC | TCGTCGCGTG | GGACGTGGTC | 150 |
| AACGAAGCGC | TGAACGACGA | TGGCACGTAT | CGGTCGGGGT | TCTACTACGA | 200 |
| CCACATCGGC | CCGACGTACA | TCGAGACGGC | GTTCCGCGCG | GCGCACACCG | 250 |
| CCGACTCGAC | GGTGCTGCTG | TCCCACAACG | ACTACAAC | | 288 |

( 2 ) INFORMATION FOR SEQ ID NO:11:

( i ) SEQUENCE CHARACTERISTICS:
        ( A ) LENGTH: 291
        ( B ) TYPE: nucleic acid
        ( C ) STRANDEDNESS: DOUBLE
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM:

( i x ) FEATURE:
    ( A ) NAME/KEY: fragment of xylanase gene from degenerate primer
        amplification of soil DNA ( x i ) SEQUENCE DESCRIPTION: SEQ ID NO:11:

| | | | | |
|---|---|---|---|---|
| CGCGGGCACA | CCGTCGTCTG | GCACGACCAG | CTCTCCACCT | GGGTGACGAC | 50 |
| GGGCAATTAC | AGCGCTGCCC | AAGCGGACTC | CATTCTCGTA | TCGTACATCA | 100 |
| CCACTGTGAT | GACGCGATAC | AAGGGTAAGG | TCGGGATCTG | GGATGTCGTC | 150 |
| AATGAAGCCA | TGGGCGATGA | TGCAGTGATC | CGCACCTCGT | CCTATTGGTA | 200 |
| TCAGAAGCTC | GGACCGAACT | ACATCGAGCG | CGCATTTCGT | CTCGCCAACA | 250 |
| GCGTTGATCC | GACGGCAAAG | CTGTCCCTCA | ACGACTACAA | C | 291 |

( 2 ) INFORMATION FOR SEQ ID NO:12:

( i ) SEQUENCE CHARACTERISTICS:
    ( A ) LENGTH: 298
    ( B ) TYPE: nucleic acid
    ( C ) STRANDEDNESS: DOUBLE
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM:

( i x ) FEATURE:
    ( A ) NAME/KEY: fragment of xylanase gene from degenerate primer
        amplification of soil DNA ( x i ) SEQUENCE DESCRIPTION: SEQ ID NO:12:

| | | | | |
|---|---|---|---|---|
| GGGCCACACG | GTGGTCTGGC | ATAACCAGAC | GCCCAAGTGG | GTCTTCGAAG | 50 |
| ACGACAAGGG | TCAACCCCTC | ACTCGCGACG | CCCTCCTCGT | CCGTCTCAAA | 100 |
| GAGCACATTA | ATAAGGTAGT | CGGCCGCTAC | AAAGGCCGTA | TCAACGGTTG | 150 |
| GGACGTCGTC | AACGAGGCCA | TCAACGAAGA | CGGCACCATG | CGCCAGTCGC | 200 |
| CCTGGATGAA | GATCATCGGC | GACGACTTCA | TCGAACTCGC | ATTCCAGTAC | 250 |
| GCGCACGACG | CCGACCCGCA | AGCCGAGCTC | TCCCACAACG | ACTACAAC | 298 |

( 2 ) INFORMATION FOR SEQ ID NO:13:

( i ) SEQUENCE CHARACTERISTICS:
    ( A ) LENGTH: 282
    ( B ) TYPE: nucleic acid
    ( C ) STRANDEDNESS: DOUBLE
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM:

( i x ) FEATURE:
    ( A ) NAME/KEY: fragment of xylanase gene from degenerate primer
        amplification of soil DNA ( x i ) SEQUENCE DESCRIPTION: SEQ ID NO:13:

| | | | | | |
|---|---|---|---|---|---|
| GGGCACACCG | TGGTCTGGCA | CTCGCAACAG | CCAGGCTGGA | TGCAGAGCCT | 50 |
| GAGCGGCACC | GCCCTGCGCA | ACGCCATGAT | CAACCATATC | AACGGCGTGA | 100 |
| TGGCCCACTA | TAAAGGCAAG | CTCGCCTACT | GGGATGTGGT | CAACGAAGCC | 150 |
| TTCGCGGACG | ACGGCAGCCA | GAACCGCCGC | AACTCGAACC | TCCAGCAGAC | 200 |
| CGGCAACGAC | TGGATCGAGG | TCGCCTTCAA | GACGGCTCGC | GCCGCCGATG | 250 |
| GCTCGGTCAA | GCTCTCCCAC | AACGACTACA | AC | | 282 |

( 2 ) INFORMATION FOR SEQ ID NO:14:

( i ) SEQUENCE CHARACTERISTICS:
        ( A ) LENGTH: 311
        ( B ) TYPE: nucleic acid
        ( C ) STRANDEDNESS: DOUBLE
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM:

( i x ) FEATURE:
        ( A ) NAME/KEY: fragment of xylanase gene from degenerate primer
            amplification of soil DNA ( x i ) SEQUENCE DESCRIPTION: SEQ ID NO:14:

| | | | | | |
|---|---|---|---|---|---|
| GCCACACGGT | GGTCTGGCAT | TCGCAGACGG | GCGGCTGGTT | CTTCCAGGGC | 50 |
| GCCGATGGTC | AGCCGGCGAC | GCGCGAAGTA | GTGATGGAGC | GGCTCCATAA | 100 |
| GCACATCACG | ACGGTCGTCG | GCCGCTACAA | AGGAAAGGTC | CTTGGGTGGG | 150 |
| ACGTCGTCAA | TGAGTCGATC | AACGACAATG | GCGACGGCAC | GACGGAAAAC | 200 |
| CTGCGGACGA | GCAGTTGGTA | TCGTGCGATC | GGGCCGGATG | TGCTGACGAT | 250 |
| GGCGTTCAAG | TGGGCGCATG | AAGCGGATCC | GGATGCGCTG | CTCTCCCTCA | 300 |
| ACGACTACAA | C | | | | 311 |

( 2 ) INFORMATION FOR SEQ ID NO:15:

( i ) SEQUENCE CHARACTERISTICS:
        ( A ) LENGTH: 300
        ( B ) TYPE: nucleic acid
        ( C ) STRANDEDNESS: DOUBLE
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM:

( i x ) FEATURE:
        ( A ) NAME/KEY: fragment of xylanase gene from degenerate primer
            amplification of soil DNA ( x i ) SEQUENCE DESCRIPTION: SEQ ID NO:15:

| | | | | | |
|---|---|---|---|---|---|
| CGGGGGCACA | CGGTGGTCTG | GCATAACCAG | ACGCCCAAGT | GGGTCTTCGA | 50 |
| AGACGACAAG | GGTCAACCCC | TCACTCGCGA | CGCCCTCCTC | GTCCGTCTCA | 100 |
| AAGAGCACAT | TAATAAGGTA | GTCGGCCGCT | ACAAAGGCCG | TATCAACGGT | 150 |
| TGGGACGTCG | TCAACGAAGC | CATCAACGAA | GACGGCACCA | TGCGCCAGTC | 200 |
| GCCCTGGATG | AAGATCATCG | GCGACGACTT | CATCGAACTC | GCATTCCAGT | 250 |
| ACGCGCACGA | CGCCGACCCG | CAAGCCGAGC | TCTCCCACAA | CGACTACAAC | 300 |

( 2 ) INFORMATION FOR SEQ ID NO:16:

( i ) SEQUENCE CHARACTERISTICS:
        ( A ) LENGTH: 288
        ( B ) TYPE: nucleic acid
        ( C ) STRANDEDNESS: DOUBLE
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM:

( i x ) FEATURE:
        ( A ) NAME/KEY: fragment of xylanase gene from degenerate primer
            amplification of soil DNA ( x i ) SEQUENCE DESCRIPTION: SEQ ID NO:16:

| | | | | | |
|---|---|---|---|---|---|
| CGGGGCCACA | CCGTCGTCTG | GCAGAACCAG | CTGCCGGACT | GGCTGACCAC | 50 |
| CGGCACCTAC | ACGTCGGCAC | AGCTGCGAGA | CCTGTTGCAC | AGGCACATCA | 100 |
| CCGACGAGGT | CTCGCACTTC | AAGGGTCACA | TCTGGCAGTG | GGATGTCGTC | 150 |
| AACGAGGCGT | TCAACGACGA | CGGCACGATG | CGGGACACCC | TCTGGCTGCG | 200 |
| CGCCATGGGC | CCTGGGTATG | TTGCCGACGC | GTTCCGCTGG | GCTCACCAGG | 250 |
| CAGATCCGGG | TGCCCTGCTC | TCCCTCAACG | ACTACAAC | | 288 |

( 2 ) INFORMATION FOR SEQ ID NO:17:

( i ) SEQUENCE CHARACTERISTICS:
        ( A ) LENGTH: 288
        ( B ) TYPE: nucleic acid
        ( C ) STRANDEDNESS: DOUBLE
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM:

( i x ) FEATURE:
        ( A ) NAME/KEY: fragment of xylanase gene from degenerate primer
            amplification of soil DNA ( x i ) SEQUENCE DESCRIPTION: SEQ ID NO:17:

| | | | | | |
|---|---|---|---|---|---|
| CGCGGGCACA | CGGTGGTGTG | GCATCAGTGT | GTGCCGGATT | GGTTAGCGAA | 50 |
| TGGAAATTTC | ACTCGCGATG | AGGCAATCGA | ACTGTTGCAC | AATCATATCT | 100 |

| | | | | |
|---|---|---|---|---|
| CGACCGTGAT | GGGACACTAC | AAGGGGCGCA | TCCTTGACTG | GGATGTGGTC | 150
| AATGAAGCGA | TTGCTGATAG | TACTCTGCTG | CGCGATACGC | CCTGGCGAAA | 200
| ATTCATCGGC | GACGACTATA | TTGAAATGGC | CTTTCGCTTC | GCCCACGAAG | 250
| CCGATCCAGA | TGCGCTCCTC | TCCCTCAACG | ACTACAAC   |            | 288

( 2 ) INFORMATION FOR SEQ ID NO:18:

( i ) SEQUENCE CHARACTERISTICS:
        ( A ) LENGTH: 282
        ( B ) TYPE: nucleic acid
        ( C ) STRANDEDNESS: DOUBLE
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM:

( i x ) FEATURE:
        ( A ) NAME/KEY: fragment of xylanase gene from degenerate primer
            amplification of soil DNA ( x i ) SEQUENCE DESCRIPTION: SEQ ID NO:18:

| | | | | |
|---|---|---|---|---|
| CGGGGGCACA | CCGTGGTGTG | GCACAAGCAA | CTGGGCGGCT | GGGTCGAACA | 50
| ACTGGACGCG | CCCGCGTTGC | GAGCCGCGCT | CGAGCACCAC | ATTCGAACCG | 100
| TCGTGGGGCA | CTACAAGGGG | AAACTCCTGG | CCTGGGACGT | CGTCAACGAG | 150
| GCCCTGGGCG | ACGACGGCAG | CCCTCGCAAG | ACGGTCTTCC | TGGAAAAGCT | 200
| GGGTCCCGGA | TACATCGCCG | ATGCGTTCCG | CTGGGCGCAT | GAGGCCGATC | 250
| CCCAGGCTCT | GTTGTCCCTC | AACGACTACA | AC         |            | 282

( 2 ) INFORMATION FOR SEQ ID NO:19:

( i ) SEQUENCE CHARACTERISTICS:
        ( A ) LENGTH: 300
        ( B ) TYPE: nucleic acid
        ( C ) STRANDEDNESS: DOUBLE
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM:

( i x ) FEATURE:
        ( A ) NAME/KEY: fragment of xylanase gene from degenerate primer
            amplification of soil DNA ( x i ) SEQUENCE DESCRIPTION: SEQ ID NO:19:

| | | | | |
|---|---|---|---|---|
| CGGGGGCACA | CGGTGGTCTG | GCATAACCAG | ACGCCCAAGT | GGGTCTTCGA | 50
| AGACGACAAG | GGTCAACCCC | TCACTCGCGA | CGCCCTCCTC | GTCCGTCTCA | 100
| AAGAGCACAT | TAATAAGGTA | GTCGGCCGCT | ACAAAGGCCG | TATCAACGGT | 150
| TGGGACGTCG | TCAACGAAGC | CATCAACGAA | GACGGCACCA | TGCGCCAGTC | 200

| GCTCTGGATG | AAGATCATCG | GCGACGACTT | CATCGAACTC | GCATTCCAGT | 250 |
| ACGCGCACGA | CGCCGACCCG | CAAGCCGAGC | TCTCCCACAA | CGACTACAAC | 300 |

( 2 ) INFORMATION FOR SEQ ID NO:20:

( i ) SEQUENCE CHARACTERISTICS:
        ( A ) LENGTH: 296
        ( B ) TYPE: nucleic acid
        ( C ) STRANDEDNESS: DOUBLE
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM:

( i x ) FEATURE:
        ( A ) NAME/KEY: fragment of xylanase gene from degenerate primer
            amplification of soil DNA ( x i ) SEQUENCE DESCRIPTION: SEQ ID NO:20:

| GGGGGCACAC | GGTGGTGTGG | CATCAACAGA | ACCCAGCGTG | GTTAACGGGC | 50 |
| ACTACGTGGA | ACGTTGACAC | ACTCAAGCTA | CTGCTCAAGG | AACACGTTGA | 100 |
| CAGCGTGGTC | GGGCATTTCA | AGGGCAAGAT | TGCCGCGTGG | GATGTCGTAA | 150 |
| ACGAAGCGTT | CAACGATGGC | ACGGGTACAC | TTCGAACAAC | GGATTCTCCG | 200 |
| TGGGCCACAA | CCATTGGGCG | TTCGTACGTT | GAACTCGCGT | TCAGAGAAGC | 250 |
| ACGCGCCATC | GATCCGGCCG | CGCAGCTGTC | CCACAACGAC | TACAAC | 296 |

( 2 ) INFORMATION FOR SEQ ID NO:21:

( i ) SEQUENCE CHARACTERISTICS:
        ( A ) LENGTH: 282
        ( B ) TYPE: nucleic acid
        ( C ) STRANDEDNESS: DOUBLE
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM:

( i x ) FEATURE:
        ( A ) NAME/KEY: fragment of xylanase gene from degenerate primer
            amplification of soil DNA ( x i ) SEQUENCE DESCRIPTION: SEQ ID NO:21:

| CGGGGCCACA | CGGTGGTCTG | GCAGAACCAG | CTACCGTCCT | GGGTGTCCAG | 50 |
| CCTGCCGCTG | AACCAGGTGC | AGCAGGCGAT | GGAAAGCCAC | ATCACCACGG | 100 |
| AGGCCAGCCA | CTACAAGGGC | CAGGTTTACG | CCTGGGACGT | CGTCAACGAG | 150 |
| CCGTTCAACG | GCGACGGCAG | CTTCGTCAGC | GATGTGTTTT | ACCGTGCGAT | 200 |
| GGGCAGCGGG | TACATCGCCG | ACGCGCTGCG | CACCGCGCAC | GCCGCCGACC | 250 |
| CCGGCGCTCA | GCTGTCCCTC | AACGACTACA | AC | | 282 |

( 2 ) INFORMATION FOR SEQ ID NO:22:

( i ) SEQUENCE CHARACTERISTICS:
        ( A ) LENGTH: 294
        ( B ) TYPE: nucleic acid
        ( C ) STRANDEDNESS: DOUBLE
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM:

( i x ) FEATURE:
        ( A ) NAME/KEY: fragment of xylanase gene from degenerate primer
            amplification of soil DNA ( x i ) SEQUENCE DESCRIPTION: SEQ ID NO:22:

```
CGGGGGCACA  CCGTGGTGTG  GTACGCGCAG  AAGCCGGCGT  CGTTCGAGCG         50

CCTGGTCAGC  GACGCCGGCG  CGTTTCGCGA  CGCCTACGCC  GCCTACATCA        100

CGGCCGTCGT  TGGCCGCTAC  AGGGGCCGCA  TCGCCGGCTG  GGGCGTCGTC        150

AACGAGCAGG  TGACCGACGA  CGGCGCCGCG  TGGCGGGACA  GCCTCTGGAG        200

CCACGCGCTC  GGACCGCTGG  AACACATGCG  CTTCGCCTAT  GAACTGGCCC        250

ACGCCGCCGA  CCCCGCGGCC  GACCTGTCCC  TCAACGACTA  CAAC              294
```

( 2 ) INFORMATION FOR SEQ ID NO:23:

( i ) SEQUENCE CHARACTERISTICS:
        ( A ) LENGTH: 285
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: Cellulomonas fimi ( i x ) FEATURE:
        ( A ) NAME/KEY: sequence of internal fragments of xylanase gene ( x i ) SEQUENCE DESCRIPTION: SEQ ID NO:23:

```
TACGGCCACA  CGCTCGTATG  GCACTCGCAG  CTGCCCGACT  GGGCGAAGAA         50

CCTCAACGGC  TCCGCGTTCG  AGAGCGCGAT  GGTCAACCAC  GTGACGAAGG        100

TCGCCGACCA  CTTCGAGGGC  AAGGTCGCGT  CGTGGGACGT  CGTCAACGAG        150

GCGTTCGCCG  ACGGCGGCGG  CCGCCGGCAG  GACTCGGCGT  TCCAGCAGAA        200

GCTCGGCAAC  GGCTACATCG  AGACCGCGTT  CCGGGCGGCA  CGTGCGGCGG        250

ACCCGACCGC  CAAGCTGTGC  ATCAACGACT  ACAAC                         285
```

( 2 ) INFORMATION FOR SEQ ID NO:24:

( i ) SEQUENCE CHARACTERISTICS:

(A) LENGTH: 1524
(B) TYPE: nucleic acid
(C) STRANDEDNESS: double
(D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
    (A) ORGANISM:

(ix) FEATURE:
    (A) NAME/KEY: sequence of xylanase gene identified by amplification of xylanase fragments from soil (xi) SEQUENCE DESCRIPTION: SEQ ID NO:24:

| ATG | ACC | GTG | AGA | TCA | ATC | CAG | AAG | AGG | CTT | CGC | GTA | TCG | CGG | CGC | 45 |
| Met | Thr | Val | Arg | Ser | Ile | Gln | Lys | Arg | Leu | Arg | Val | Ser | Arg | Arg | |
| GGC | GGT | GGC | GCC | CGC | GCC | GGC | CGG | CCA | CGT | CAA | CAG | GTG | CTG | ACA | 90 |
| Gly | Gly | Gly | Ala | Arg | Ala | Gly | Arg | Pro | Arg | Gln | Gln | Val | Leu | Thr | |
| GCG | GTG | GCG | GCG | ACT | GCC | TGC | GTC | GCG | GGC | GGC | GCG | CTC | GCC | GCG | 135 |
| Ala | Val | Ala | Ala | Thr | Ala | Cys | Val | Ala | Gly | Gly | Ala | Leu | Ala | Ala | |
| GCA | GTG | CTG | GCC | GCG | GCC | GGG | CCG | GCC | ACG | GCG | GCC | GGC | AGC | ACG | 180 |
| Ala | Val | Leu | Ala | Ala | Ala | Gly | Pro | Ala | Thr | Ala | Ala | Gly | Ser | Thr | |
| CTG | CGG | GCG | GCG | GCT | GAG | GCG | CAG | GGC | AAG | TAC | TTC | GGG | ACT | GAG | 225 |
| Leu | Arg | Ala | Ala | Ala | Glu | Ala | Gln | Gly | Lys | Tyr | Phe | Gly | Thr | Glu | |
| GTC | ACC | GGG | AAC | ATG | ATC | AAC | AAC | TCG | ACG | ATC | ACG | AAC | CTG | GCA | 270 |
| Val | Thr | Gly | Asn | Met | Ile | Asn | Asn | Ser | Thr | Ile | Thr | Asn | Leu | Ala | |
| GGC | CAG | CAG | TTC | GAC | ATG | GTC | ACC | CCG | GGC | AAC | GAG | ATG | AAG | TGG | 315 |
| Gly | Gln | Gln | Phe | Asp | Met | Val | Thr | Pro | Gly | Asn | Glu | Met | Lys | Trp | |
| GAC | ACC | ACC | GAG | CCG | TCC | AAC | GGG | TCC | TAC | AAC | TTC | GGC | CCG | GGC | 360 |
| Asp | Thr | Thr | Glu | Pro | Ser | Asn | Gly | Ser | Tyr | Asn | Phe | Gly | Pro | Gly | |
| GAC | GCG | GTC | GTG | TCG | TTC | GCC | AAG | GCG | CAC | GGC | ATG | CGG | GTG | CGC | 405 |
| Asp | Ala | Val | Val | Ser | Phe | Ala | Lys | Ala | His | Gly | Met | Arg | Val | Arg | |
| GGG | CAC | AAC | CTG | GTC | TGG | CAG | AAC | CAG | CTC | CCG | TCG | TGG | GTT | TCC | 450 |
| Gly | His | Asn | Leu | Val | Trp | Gln | Asn | Gln | Leu | Pro | Ser | Trp | Val | Ser | |
| AGC | CTG | CCG | CTG | AAC | CAG | GTG | CAG | CAG | GCG | ATG | GAA | AGC | CAT | GTC | 495 |
| Ser | Leu | Pro | Leu | Asn | Gln | Val | Gln | Gln | Ala | Met | Glu | Ser | His | Val | |
| ACC | ACG | GAG | GCC | AGC | CAC | TAC | AAG | GGC | CAG | GTT | TAC | GCC | TGG | GAC | 540 |
| Thr | Thr | Glu | Ala | Ser | His | Tyr | Lys | Gly | Gln | Val | Tyr | Ala | Trp | Asp | |
| GTC | GTC | AAC | GAG | CCG | TTC | AAC | GGC | GAC | GGC | AGC | TTC | GTC | AGC | GAC | 585 |
| Val | Val | Asn | Glu | Pro | Phe | Asn | Gly | Asp | Gly | Ser | Phe | Val | Ser | Asp | |
| GTG | TTT | TAC | CGC | GCG | ATG | GGC | AGC | GGG | TAC | ATC | GCC | GAC | GCG | CTG | 630 |
| Val | Phe | Tyr | Arg | Ala | Met | Gly | Ser | Gly | Tyr | Ile | Ala | Asp | Ala | Leu | |
| CGC | ACC | GCG | CAC | GCC | GCC | GAC | CCC | AGT | GCC | CAG | CTG | TAC | ATC | AAC | 675 |
| Arg | Thr | Ala | His | Ala | Ala | Asp | Pro | Ser | Ala | Gln | Leu | Tyr | Ile | Asn | |
| GAC | TAC | AGC | ATC | GAG | GGC | GAG | AAC | GCC | AAG | AGC | AAC | GCC | ATG | TAC | 720 |
| Asp | Tyr | Ser | Ile | Glu | Gly | Glu | Asn | Ala | Lys | Ser | Asn | Ala | Met | Tyr | |
| AGC | CTG | GTG | CAG | TCC | CTG | CTG | GCG | CAG | GGG | GTG | CCG | ATC | AAC | GGC | 765 |
| Ser | Leu | Val | Gln | Ser | Leu | Leu | Ala | Gln | Gly | Val | Pro | Ile | Asn | Gly | |
| GTG | GGC | TTT | GAA | AGC | CAC | TAC | ATC | GTG | GGG | CAG | GTG | CCC | TCG | TCG | 810 |
| Val | Gly | Phe | Glu | Ser | His | Tyr | Ile | Val | Gly | Gln | Val | Pro | Ser | Ser | |
| CTG | CTG | GCC | AAC | ATG | CAG | CGG | TTC | GCT | GCC | CTG | GGC | GTC | AAC | GTG | 855 |
| Leu | Leu | Ala | Asn | Met | Gln | Arg | Phe | Ala | Ala | Leu | Gly | Val | Asn | Val | |
| GCG | GTC | ACC | GAG | CTT | GAC | GAC | CGC | GTC | CAG | CTG | CCG | GCC | AGC | ACC | 900 |

-continued

| | | | | | | | | | | | | | | | | |
|---|---|---|---|---|---|---|---|---|---|---|---|---|---|---|---|---|
| Ala | Val | Thr | Glu | Leu | Asp | Asp | Arg | Val | Gln | Leu | Pro | Ala | Ser | Thr | | |
| GCG | AGC | CTG | AAC | CAG | CAG | GCC | ACC | GAC | TAC | GCC | ACC | GTG | GTG | CGC | | 945 |
| Ala | Ser | Leu | Asn | Gln | Gln | Ala | Thr | Asp | Tyr | Ala | Thr | Val | Val | Arg | | |
| GAC | TGC | CTG | CAG | GTC | TCC | CGC | TGC | GTC | GGC | GTG | TCG | CAA | TGG | GGC | | 990 |
| Asp | Cys | Leu | Gln | Val | Ser | Arg | Cys | Val | Gly | Val | Ser | Gln | Trp | Gly | | |
| GTC | GGC | GAC | GCC | GAC | TCC | TGG | ATC | CCG | GGA | ACG | TTC | CCC | GGC | TGG | | 1035 |
| Val | Gly | Asp | Ala | Asp | Ser | Trp | Ile | Pro | Gly | Thr | Phe | Pro | Gly | Trp | | |
| GGC | GCG | GCG | ACC | ATG | TAC | GAC | CAG | AAC | TAC | CAG | CCC | AAG | CCC | GCG | | 1080 |
| Gly | Ala | Ala | Thr | Met | Tyr | Asp | Gln | Asn | Tyr | Gln | Pro | Lys | Pro | Ala | | |
| TAC | TCC | GCC | ACC | TTG | TCC | GCC | CTC | GGC | GGC | TCC | GGC | AGC | ACC | GGC | | 1125 |
| Tyr | Ser | Ala | Thr | Leu | Ser | Ala | Leu | Gly | Gly | Ser | Gly | Ser | Thr | Gly | | |
| GGT | GGC | AGC | GGC | GAG | ATC | CAC | GCG | GTC | GGG | GCG | GGC | AAG | TGC | CTG | | 1170 |
| Gly | Gly | Ser | Gly | Glu | Ile | His | Ala | Val | Gly | Ala | Gly | Lys | Cys | Leu | | |
| GAC | GTG | CCC | GGC | CTC | GCC | ACC | ACC | GCG | GGC | ACC | CAG | CTG | GAC | ATC | | 1215 |
| Asp | Val | Pro | Gly | Leu | Ala | Thr | Thr | Ala | Gly | Thr | Gln | Leu | Asp | Ile | | |
| TGG | ACC | TGC | AAC | GGC | GGC | ACC | AAC | CAG | ATC | TGG | ACG | CAC | ACC | TCC | | 1260 |
| Trp | Thr | Cys | Asn | Gly | Gly | Thr | Asn | Gln | Ile | Trp | Thr | His | Thr | Ser | | |
| GCC | AAC | CAG | CTG | ACC | GTC | TAC | AGC | GGC | AGC | AGC | CAG | ATG | TGC | CTG | | 1305 |
| Ala | Asn | Gln | Leu | Thr | Val | Tyr | Ser | Gly | Ser | Ser | Gln | Met | Cys | Leu | | |
| GAC | GCT | TAC | AAC | AAC | CAG | ACC | ACC | CCC | GGC | ACC | AAG | GTG | GAC | ATC | | 1350 |
| Asp | Ala | Tyr | Asn | Asn | Gln | Thr | Thr | Pro | Gly | Thr | Lys | Val | Asp | Ile | | |
| TGG | ACG | TGC | AAC | GGC | GGC | GCT | AAC | CAG | CAG | TGG | CAC | GTC | AAC | TCC | | 1395 |
| Trp | Thr | Cys | Asn | Gly | Gly | Ala | Asn | Gln | Gln | Trp | His | Val | Asn | Ser | | |
| AAC | GGC | ACG | ATC | ACC | AGT | GCC | CAG | TCC | GGG | CTG | TGC | CTG | GAC | GTG | | 1440 |
| Asn | Gly | Thr | Ile | Thr | Ser | Ala | Gln | Ser | Gly | Leu | Cys | Leu | Asp | Val | | |
| ACC | GGC | GCC | AGC | ACC | GCC | AAC | GGC | GCG | CTG | GCC | GAG | CTG | TGG | ACC | | 1485 |
| Thr | Gly | Ala | Ser | Thr | Ala | Asn | Gly | Ala | Leu | Ala | Glu | Leu | Trp | Thr | | |
| TGC | AAC | AGC | CAG | TCC | AAC | CAG | CAA | TGG | ACC | CTC | GGA | TGA | | | | 1524 |
| Cys | Asn | Ser | Gln | Ser | Asn | Gln | Gln | Trp | Thr | Leu | Gly | *** | | | | |

METHOD FOR ISOLATING XYLANASE GENE SEQUENCES FROM SOIL DNA, COMPOSITIONS USEFUL IN SUCH METHOD AND COMPOSITIONS OBTAINED THEREBY

This application claims priority under the provisions of 35 USC § 119 (e)(1) from U.S. Provisional Application Ser. No. 60/004,157 filed Sep. 22, 1995.

FIELD OF THE INVENTION

This application relates to the use of PCR amplification to isolate novel xylanase genes from soil DNA, and to primers useful in such methods and the products obtained thereby.

BACKGROUND OF THE INVENTION

The hydrolysis of cellulose, and hemicellulose, with xylans being a major component of hemicellulose, requires a variety of enzymes having activity as endoglucanases, exoglucanases, and xylanases to work in concert. It is with these systems of enzymes, composed of enzymes from the different cellulase families, that plant material is degraded in nature.

Cellulases have been classified into 12 families designated A to L), and a single organism may have a set of enzymes with members drawn from several families. Of these families, families F and G show xylanase activity.

There has been an increasing awareness of the potential industrial uses for cellulases and xylanases; examples include biomass conversion, Saddler, J. N., *Bioconversion of forest and agricultural plant residues,* CAN International, Oxford, England (1993), and the role cellulases and xylanases are playing in pulp processing and paper production. Wick, C. B., *Genetic Engineering news* 14: 10–11 (1994). For example, xylanases can be used to make pulp bleaching more environmentally friendly by reducing organochlorine discharges. McCubbin, N., *Pulp & Paper Canada,* 95: 4 (1994).

In identifying and characterizing cellulases and xylanases suitable for use in industry, traditional methods of isolation and selection of cellulase and xylanase-producing organisms continues to be carried out by growth on cellulose and cellulose-like substrates. However, the traditional methods are only suitable for culturable organisms. Considering that it is estimated that only 1% of the organisms present in soil are culturable, Tiedje, J. M., *ASM News* 60:524–525 (1994), these traditional methods only skim the surface of the resource of enzymes which soil could theoretically provide.

Bergquist et al., in a paper delivered at the Society for Industrial Microbiology Meeting in Montreal, Canada in June 1994 discussed methods for isolating hemicellulolytic enzymes from the extremely thermophilic bacteria in hot pools having temperatures as high as 95° C. For non-culturable organisms, they suggest that the polymerase chain reaction (PCR) on total DNA isolated from concentrated hot springs water with primers hybridizing to conserved regions of the known xylanase genes can be used to isolate xylanase DNA. Bergquist did not disclose or suggest methods for recovery of xylanase DNA from far more complex and challenging soil samples.

It is an object of the present invention to provide access to the cellulase and xylanase enzymes produced by non-culturable organisms by providing a mechanism for extracting DNA specific to Family F xylanases from soil.

It is a further object of this invention to provide specific compositions, particularly primers, useful in performing this isolation procedure.

It is still a further object of the invention to provide novel xylanase enzymes containing active sites which have been isolated from soil using the procedures of the present invention.

SUMMARY OF THE INVENTION

The present invention provides a method for recovering xylanase-encoding DNA from soil, comprising the steps of:

(a) treating a soil sample to render DNA in the soil accessible for hybridization with oligonucleotide primers;

(b) combining the treated soil sample with first and second primers in an amplification reaction mixture, said first and second primers hybridizing with conserved regions of the sense and antisense strands respectively of a gene encoding a xylanase and flanking a region of interest in the gene;

(c) thermally cycling the amplification reaction mixture through a plurality of cycles each including at least a denaturation phase and a primer extension phase to produce multiple copies of the region of interest flanked by the primers; and (d) recovering the copies of the region of interest from the amplification reaction mixture. Because of the complexity of the soil samples, it is likely that the recovered product will include more than one species of polynucleotide. Thus, these recovered copies may, in accordance with the invention, be cloned into a host organism to produce additional copies of each individual species prior to characterization by sequencing.

Recovered DNA which is found to vary from known xylanases can be used in several ways to facilitate production of novel xylanases for industrial application. First, the recovered DNA, or probes corresponding to portions thereof, can be used as a probe to screen soil DNA libraries and recover intact xylanase genes including the unique regions of the recovered DNA. Second, the recovered DNA or polynucleotides corresponding to portions thereof, can be inserted into a known xylanase gene to produce a recombinant xylanase gene with the sequence variations of the recovered DNA.

BRIEF DESCRIPTION OF THE DRAWINGS

FIG. 2 shows the sequence differences between twenty DNA fragments isolated using the method of the invention and the sequence of the corresponding region of the Family F xylanase from *Cellulomonas fimi.*

DETAILED DESCRIPTION OF THE INVENTION

Figure 1:
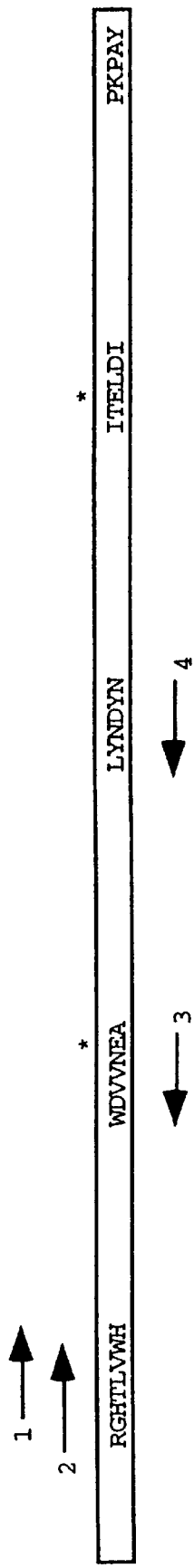
FIG. 1 shows a map of a Family F xylanase gene showing the location of conserved regions suitable for use as primers.

Although the method of the invention for recovering xylanase DNA from soil samples appears in retrospect to be similar to PCR amplification of DNA from other sources (including the hot spring water of Bergquist et al.), the utility of PCR amplification in this environment and for this purpose could not be predicted with any confidence because of the complexity of soil. Soil is a complex mixture of minerals, decaying organic matter, and numerous organisms and microorganisms. As such it contains many possible sources of DNA, and many complex organic materials, e.g., humic materials, which could interfere with primer binding or polymerase enzyme activity to make PCR amplification unworkable. Thus, the very first question addressed in the development of the present invention was whether or not PCR amplification could be performed directly on a soil sample.

To determine whether PCR could be effectively used to amplify Family F cellulase gene fragments in the presence of humic substances carried over into extracted soil samples, soil DNA prepared by direct lysis as described in Barns, et al., *Proc. Natl. Acad. Sci.* 91: 1609–1613 (1994), was spiked with *Cellulomonas fimi* genomic DNA, and PCR was performed using degenerate primers hybridizing to conserved regions of Family F xylanase genes (FIG. 1) and processed in two rounds of PCR, for a total of 70 cycles. Agarose gel electrophoresis was used to separate the PCR products. Evaluation of these gels clearly showed two bands corresponding to about 300 and 400 base pairs for the spiked samples and for an undiluted genomic control. The lower band is the expected size (285 bp) from *C. fimi* genomic DNA. The 400 bp band upon further investigation yielded a putative second family F cellulase member enzyme for *C. fimi*. With increasing dilution of the genomic DNA, more distinct PCR products appear in the regions outside of the 400 bp and 300 bp regions. Overall, these results indicate that the humic substances are not appreciably inhibiting the PCR, and PCR products could be obtained without optimization. In addition, at greater dilutions of the genomic DNA, the target sequences in the soil DNA experience less competition from the genomic DNA for primer binding. This leads to amplification of soil DNA targets.

Since the preliminary experiments showed that PCR could be used to amplify soil DNA, PCR was performed on unspiked soil DNA. In this case, PCR amplification resulted in the amplification of five bands greater than 300 bp. This result is not unexpected as the size of the fragments of family F cellulases that the constructed primers target, in known family F members, are quite heterogeneous, with variation between 195 bp and 345 bp, and further evaluation of the recovered fragments confirmed that the products are likely to be xylanase gene fragments based on homology to known genes. Thus, in accordance with the present invention there is provided a method for recovering xylanase DNA from soil, comprising the steps of:

(a) treating a soil sample to render DNA in the soil accessible for hybridization with oligonucleotide primers;

(b) combining the treated soil sample with first and second primers in an amplification reaction mixture, said first and second primers hybridizing with conserved regions of the sense and antisense strands respectively of a gene encoding a xylanase and flanking a region of interest in the gene;

(c) thermally cycling the amplification reaction mixture through a plurality of cycles each including at least a denaturation phase and a primer extension phase to produce multiple copies of the region on interest flanked by the primers; and (d) recovering the copies of the region of interest from the amplification reaction mixture.

The soil sample employed in the present invention may be any type of soil that includes a mixture of mineral and organic materials. In the initial step of the method of the invention, a soil sample is treated to render the DNA accessible to the primers and enzymes employed in the amplification reaction. For example, DNA can be rendered accessible by a direct lysis procedure in which soil is treated with lysozyme, followed by Proteinase K, and then extracted with an organic solvent. DNA is precipitated from the aqueous phase and then further purified by chromatography. Incorporation of soil DNA into a phage library can also be performed, and such a library is a form of a treated soil sample within the scope of the present invention.

The treated soil sample is combined with two primers for PCR amplification in an amplification reaction mixture. The basic requirements for PCR amplification are well known, for example from U.S. Pat. No. 4,683,202 of Mullis, which is incorporated herein by reference and will not be described in detail. In general, however, the amplification reaction will include a thermostable polymerase enzyme such as Taq or Ultratherm™ polymerase and all four types of nucleotide triphosphates (A, C, G and T) in a buffer suitable for primer extension reactions.

The primers employed in the method of the invention can be any pair of primers which bind to conserved regions on complementary strands of a cellulase/xylanase gene and which flank a region of interest because of suspected structural diversity. FIG. 1 shows the location of the primers used by Bergquist et al. to amplify xylanase gene fragments from hot spring waters, which could be used to amplify soil DNA, and a preferred set of primers which produce larger fragments. These preferred primers are degenerate primers having the sequences forward primer:
CGS GGS CAC ACS XTS XTS TGG [SEQ ID NO 1],
and reverse primer:
GTT GTA GTC GTT GWX GXA SA [SEQ ID NO 2],
where S indicates a C or G, W indicates an A or T, and X indicates an inosine.

The amplification reaction mixture containing the primers and the treated soil sample is subjected to a plurality of thermal cycles to produce amplified DNA fragments corresponding to the region flanked by the primers. After thermal cycling, the amplification products are separated on an electrophoresis gel. Agarose gels have been found to be sufficient for this purpose, although polyacrylamide gels could also be used. Other separation techniques, including capillary electrophoresis and the use of biotinylated primers to facilitate capture of the amplified materials on an (strept) avidin-coated support might also be employed to recover the amplified DNA from the reaction mixture.

Because of the diversity of DNAs in soil samples, the products produced in the amplification reaction are likely to include more than one species of xylanase gene fragment. Thus, the recovered DNA is suitably cloned in a host organism to produce multiple copies of each species individually. We have used Invitrogen's "Original TA cloning kit" that utilizes 3' A overhangs on the PCR product for ligation for cloning the amplified fragment into pCRII. This plasmid was then introduced into *E. coli* INVαF' by conventional means. The specific plasmid and host organism are not critical, however, and other plasmids and hosts could be also be used.

Plasmids containing the cloned soil DNA are recovered from the host organisms and evaluated by sequencing, preferably using a modification of the Sanger et al method. Sequencing primers that are the same as or similar to the original amplification primers can be used to obtain the sequence of the region flanked by the amplification primers, as can primers that hybridize with portions of the plasmid. Sequencing can be carried out using labeled primers or dye-labeled chain-terminating nucleotide triphosphates. The sequences determined are compared to known sequences for xylanase genes, for example using the BLAST program, to confirm that cloned fragment is derived from a xylanase gene and to determine whether it has a previously uncharacterized sequence. Unique xylanase sequences are then further processed to obtain a complete gene of unique sequence for evaluation.

The process of obtaining a complete xylanase gene can be carried out in two ways. First, the recovered DNA, or selected portions thereof which contain unique base sequences can be used to select xylanase genes from a phage library containing soil DNA. While it will be understood that the specific techniques and reagents employed in construction of a library permit the exercise of a great many personal preferences, we constructed a library from soil DNA prepared by a modification of the method described by Holben et al., *Appl. Environ Microbiol.* 53: 703–711 (1988). In this process, soil samples are homogenized and the centrifuged at progressively greater g to isolate a bacterial pellet. The pellet is suspended in buffer, treated with Sarkosyl and then lysed with lysozyme. The lysed cells are treated with pronase followed by Sarkosyl. DNA is extracted from the bacterial lysate supernatant by a standard phenol/chloroform extraction and then precipitated by isopropanol. The DNA was further purified by centrifugation through Sephadex G-200 columns as follows.

The resulting soil DNA was partially digested (less than 20 minutes exposure to the enzyme) with 0.5 units of restriction endonuclease BstY I per ug of DNA and loaded on an 0.3% agarose gel from which 6 to 12 kilobase fragments were electroeluted. The ligation, packaging, and amplification protocols were followed as per Stratagene's Predigested ZAP Express BamHI/CIAP Vector Cloning Kit, and the GIGAPACK III Gold Packaging Extract. The ligation was carried out with a 1 to 5 molar ratio of vector to insert DNA.

The resulting library is then screened to identify members of the library containing xylanase genes using probes based upon the novel sequences found from the initial amplification of soil DNA. The probe sequence may be the full length polynucleotide produced by amplification of the soil DNA and cloning. Alternatively, the probe sequence may be a polynucleotide which includes one or more of the unique genetic variations detected in the amplified products, in an otherwise known xylanase gene fragment. Probes used in this step may have lengths in the range of from 20 to 1500 bases, preferably 100 to 1000 bases.

Once identified, phagemids containing the selected xylanase inserts can be recovered and evaluated. The xylanase insert can, for example, be sequenced using primer walking over the inset to confirm the presence of the desired variation, or may be expressed and the expressed enzyme evaluated to determine the properties of the enzyme encoded by the insert.

As an alternative to the use of probes to isolate naturally occurring enzymes which deviate from the standard xylanase sequences, constructed xylanase genes can be formed using techniques such as site-directed mutagenesis or PCR-directed domain shuffling (See Crameri et al., *Nature Biotechnology* 14: 315–319 (1996), to introduce one or more sequence variations corresponding to variations found in amplified soil sample DNA. General techniques for introducing defined variations into known sequences are well known in the art, and will not be repeated here.

Figure 2:
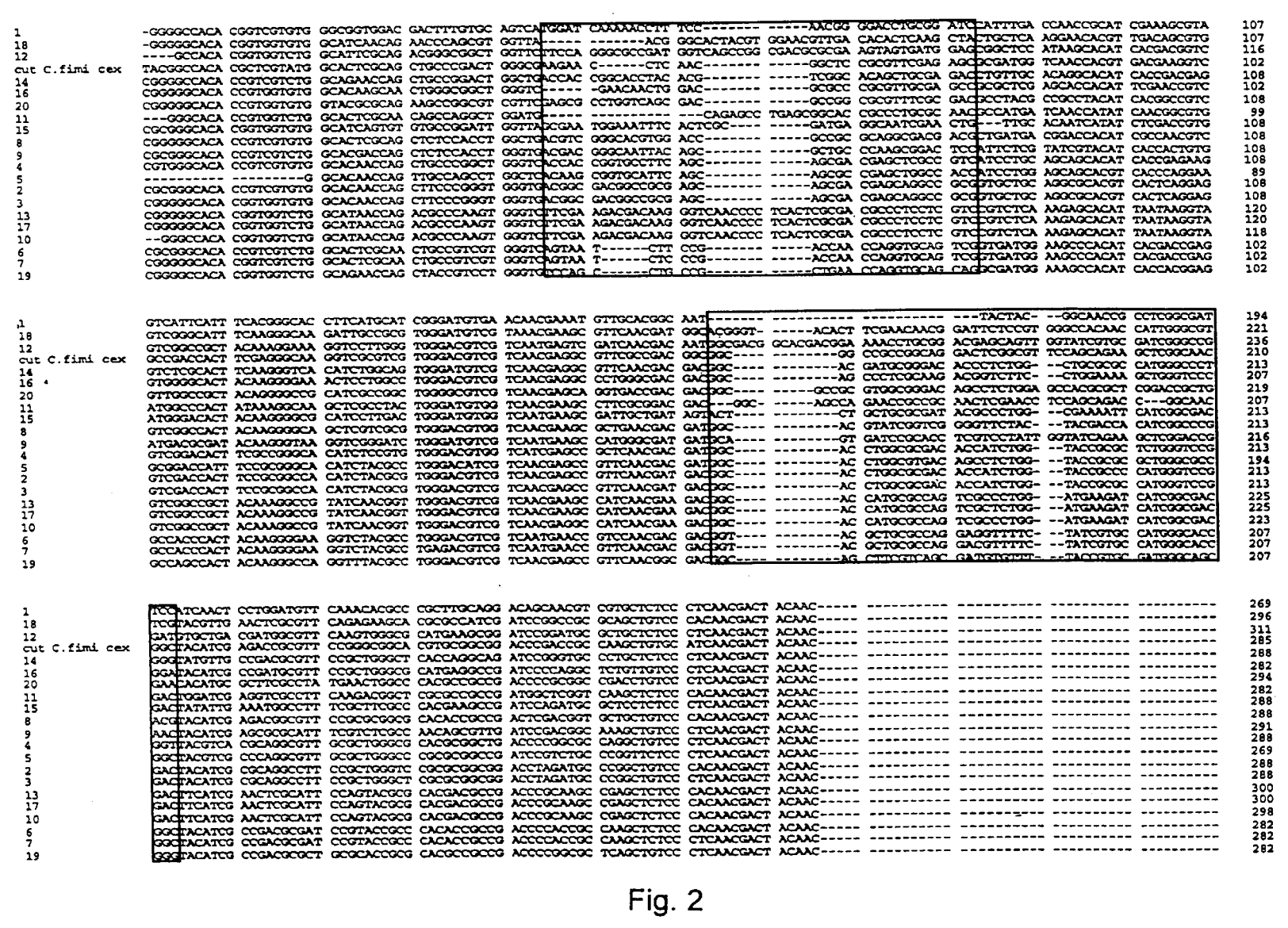

Using the method of the invention, the present inventors have isolated and sequenced a total of twenty different xylanase DNA fragments that do not correspond to previously known xylanases and one complete novel xylanase gene. The sequences of these fragments and gene are given Seq. ID Nos. 3–22. FIG. 2 shows a comparison of the fragment sequences with the corresponding region of the xylanase from *C. fimi* (Seq. ID No. 23), with boxes drawn around regions containing regions of significant variability. Polynucleotides including one or more of these variations, and particularly polynucleotides including the boxed regions, can be utilized in designing probes or recombinant genes as discussed above.

The invention will now be further described with reference to the following non-limiting examples.

EXAMPLE 1

DNA was extracted from a soil sample using the "direct lysis" method as described in Barns et al., *Proc. Natl. Acad. Sci.* 91: 1609–1613 (1994). The resulting extracted soil sample was combined with two degenerate primers targeting highly conserved regions of family F cellulases, namely:

5'-CG(CG) GG(CG) CAC AC(CG) XT(CG) XT(CG) TGG-3' [Seq ID No 1]

and

5'-GTT GTA GTC GTT G(AT)X GXA (CG)A-3' [Seq ID No. 2]

where "X" indicates an inosine. Inosine was used to decrease the degeneracy of each primer. Patil, et al., *Nucleic Acid Res.* 18: 3080 (1990). These primers flank an active site of Family F cellulases such that variations in recovered sequences are likely to be significant to the function of the enzyme.

Amplification was performed on a MJResearch PTC-100 thermocycler as follows: 25–80 ng of template DNA, 0.50 ug of each primer, 50 $\mu$M of each dNTP, 1.5 mM of $MgCl_2$, 1× of 10× Taq buffer, and 5U of Taq polymerase (buffer and polymerase from GibcoBRL), were mixed with sterile distilled water to 50 ul. Following a "hotstart" of 94° C. for 3 min, cooling the mix in ice for 5 min, centrifuging, and maintaining at 80° C. while loading the polymerase, a "touchdown" protocol was utilized to overcome the Tm difference of the primers and to prevent spurious priming. Don, et al., *Nucleic Acids Res.* 19: 4008 (1991); Roux, K. H., *BioTechniques* 16: 812–814 (1994). Thermocycling: denaturation, 94° C. for 50 sec; annealing, 65° C. for 1 min; extension, 72° C. for 1 min; and for the first 10 cycles, the annealing temperature was lowered 1° C. per cycle until 55° C. was reached. Then a subsequent 25 cycles were carried out with the annealing temperature at 55° C. A final extension for 10 min at 72° C. was carried out. PCR products were analyzed by electrophoresis through a 1.5% agarose gel with ethidium bromide staining.

DNA was extracted from agarose gel by the QIAGEN Qiaex protocol, or by the "freeze-thaw" method involving the steps of: excision of the DNA band from the gel, freezing at −80° C. for 20 min, thawing at 37° C. for 10 min, the addition of 10 ul of $H_2O$, centrifugation at 15000 rpm in a minifuge for 2 min, then removing and saving the liquid. The extracted DNA was reamplified using the same primers, separated on an agarose gel and then cloned into pCRII plasmid using the Invitrogen "Original TA cloning kit." The plasmids were transformed into Invitrogen's competent *E. coli* cells.

Selection of cells containing transformed plasmids was performed by growth on LB media containing ampicillin and X-gal. White colonies were selected, and after overnight growth, cloned plasmids were purified using either QIAwell 8, or tip-20 modified alkaline lysis, and resin plasmid extraction and purification kits (from QIAGEN Inc.) and sequenced using an Applied Biosystems, Inc. PRISM Ready Reaction DyeDeoxy Terminator Cycle Sequencing Kit on an ABI 373 Stretch sequencer. Geneworks (by IntelliGenetics Inc.), Apple Mac version, was used for resolving sequence ambiguities, translation, and alignment construction. The determined DNA sequences were sent to the NCBI BLAST database located at, e-mail: blast@ncbi.nlm.nih.gov for the comparison of DNA sequences against protein databases.

Using this method, eight DNA fragments, denominated herein as Seq. ID. No. 3 through 10 were identified. Blast analysis confirmed the assignment of these fragments as derived from a xylanase gene, but did not produce an exact match for any of the fragments.

EXAMPLE 2

The experiment of example 1 was repeated except that different PCR reagents and conditions were used. In place of Taq polymerase, 1U of ULTRATHERM™ from BIO/CAN was used, and processed at a lower annealing temperature to see if this would generate a more diverse set of fragments. The thermocycling program used was: 94° C. for 30 seconds; 45° C. for 1 minute; increase temperature 1° C. per 5 seconds to 72° C.; 72° C. for 45 seconds; repeat the previous steps 4 times, each time increasing the annealing temperature by 2° C.; carry out 10 cycles of 94° C. for 30 seconds, 53° C. for 1 minute, 72° C. for 45 seconds; then 94° C. for 30 seconds, 55° C. for 1 minute, increase temperature 1° C. per 5 seconds to 72° C. and 72° C. for 45 seconds; then 30 cycles of 94° C. for 30 seconds, 55° C. for 1 minute, 72° C. for 45 seconds; and a final extension step of 72° C. for 10 minutes. This resulted in the recovery of an additional ten fragments denominated as Seq. ID Nos. 11 through 20 herein.

EXAMPLE 3

To prepare a phage library, soil DNA was first prepared by homogenizing a 50 g soil sample in a homogenization buffer containing 1.43 mM $K_2HPO_4$, 1.01 mM $MgSO_4 \cdot 7 H_2O$, 2.14 mM NaCl, 4.75 uM $Fe_2(SO_4)_3 \cdot 7 H_2O$, 14.8 uM $MnSO_4 \cdot 4 H_2O$ to which sodium ascorbate was added just before use to achieve a final concentration of 0.2M. The homogenate was filtered through cheese cloth and the recovered solids suspended in 100 mL TE buffer to form a bacterial suspension. The suspension was brought to 1M NaCl by addition of 25 mL of 5M NaCl, incubated at room temperature for 10 minutes and then collected by centrifugation. The pellet was resuspended in TS buffer (50 mM Tris, pH 8.0; 50 MM NaCl) transferred to a 50 mL polycarbonate centrifuge tube and brought to a concentration of 0.1% Sarkosyl by addition of 50 uL of 20% Sarkosyl. This mixture was incubated at room temperature for 10 minutes, after which the bacteria were collected by centrifugation. The bacterial pellet was drained and suspended in 35 m: of Tris-sucrose-EDTA which contains 0.75M sucrose, 50 mM Tris (pH 8.0) and 10 mM EDTA. Lysozyme was added to a final concentration of 5 mg/ml and the samples were incubated at 37° C. for 60 minutes. A pronase solution in TS buffer that had been predigested by incubation for 30 minutes at 37° C. was added to the bacteria-lysozyme mixture, mixed by vortexing, and then incubated at 37° C. for 60 minutes. The temperature was then raised to 65° C. and 0.25 ml 20% Sarkosyl was added and incubated for 10 minutes. DNA was extracted from the supernatant of the resulting bacterial lysate by a standard phenol/chloroform extraction. The DNA was then precipitated by isopropanol. The DNA was further purified by centrifugation through SEPHADEX G-200 columns as follows.

2 grams of SEPHADEX G-200 (Pharmacia Biotech) were washed 5 times with 75 ml TE Buffer pH 8.0 (10 mM Tris-HCl, 1 mM EDTA). Each time, the mixture was allowed to settle and excess TE drawn off before adding more TE. Then the SEPHADEX suspension was autoclaved. Excess TE was drawn off and the suspension brought to the original volume with high salt TE buffer pH 8.0 (10 mM Tris-HCl, 1 mM EDTA, 0.1M NaCl), shaken and allowed to settle. Excess TE was drawn off and the suspension was again brought to the original volume with high salt TE buffer, and shaken again. A 5 ml syringe was packed with sterile fiberglass to the 1 cc mark, and SEPHADEX added. This column was then spun in a swing-bucket centrifuge for 10 minutes at 1000 × g in a sterile test tube, 500 ul of the high-salt TE was added, and the column was spun again for 10 minutes at 1000 × g. The column was then transferred to a new test tube, the DNA added to the column, and spun for 10 minutes at 1000 × g. For three more times, 500 ul of the high-salt TE was added and the column spun for 10 minutes at 1000 × g. A final dry spin for 10 minutes at 1000 × g was carried out. The DNA was then precipitated with 1/10 volume of 3M Sodium Acetate and two volumes of 95% Ethanol. The suspension was held over night at 4° C. This was then centrifuged for 20 minutes in a minifuge at 4° C., the supernatant was removed and replaced with 70% Ethanol and re-centrfuged. The supernatant was removed and the pellet was dried, and dissolved in TE (not high-salt).

The resulting soil DNA preparation was partially digested (less than 20 minutes exposure to the enzyme) with 0.5 Units of BstYI per ug of DNA and 6 to 12 kilobase fragments were electroeluted from 0.3% agarose gel. The ligation, packaging, and amplification protocols were followed as per Stratagene's Predigested ZAP Express BamHI/CIAP Vector Cloning Kit, and the Gigapack III Gold Packaging Extract. The ligation was carried out with a 1 to 5 molar ratio of vector to insert DNA.

Although probes having sequences derived from any of Seq ID Nos. 3 to 20 could have been used to screen the library, we chose to prepare additional probes by PCR amplification of the library stock. 5 ul of a $1.1 \times 10^5$ pfu/ul library stock, 50 uM final concentration of each dNTP, 0.5 uM final concentration of each degenerate primer (Seq. ID Nos. 1 and 2), 1.5 mM final concentration of $MgCl_2$, 10% DMSO, 1× of 10× ULTRATHERM buffer, 1U of ULTRATHERM polymerase (buffer and polymerase from BIO/CAN Scientific, Ontario, Canada), and sterile, distilled water were mixed. Thermocycling: 94° C. for 50 seconds; 65° C. for 1 minute; 72° C. for 1 minute; and for the first 10 cycles, the annealing temperature was lowered 1° C. per cycle until 55° C. was reached. A subsequent 35 cycles were carried out with the annealing temperature at 55° C., then a final extension for 10 minutes at 72° C. The Invitrogen "Original TA cloning kit" was used for cloning as in Example 1. Extra ATP was added to a final concentration of 1 mM. Plasmid DNA was extracted and purified with QIAGEN's tip-20 kit. The probe was prepared by digesting the TA vector with insert, with EcoRI. The digested sample was electrophoresed through a 1.2% agarose gel with ethidium bromide staining. The band of interest was cut out of the gel and the DNA fragment purified using QIAGEN's QIAEX kit. This procedure led to the identification of two additional xylanase fragments, denominated herein as Seq. ID Nos. 21 and 22. The fragment was labeled using GibcoBRL's Random Primers DNA Labeling System with $[\alpha^{-32}P]dCTP$ as per provided protocol.

EXAMPLE 4

Screening of the library was performed using the fragment with the sequence given by Seq. ID. No. 21 as a probe.

The screening protocol supplied with Stratagene's Predigested ZAP Express BamHI/CIAP Vector Cloning Kit was followed. The post-hybridization washes were as follows: two washes in 0.5× SSC, 0.1% (w/v) SDS at 55 C; followed by one 0.5× SSC, 0.1% (w/v) SDS wash at 60 C. Next, Stratagene's recommended in vivo excision protocol was followed to isolate E. coli colonies containing the pBK-CMV phagemid with insert DNA. Phagemid DNA with insert was extracted and purified with QIAGEN's tip-20 kit.

EXAMPLE 5

A xylanase gene contained in a phagemid from the library was sequenced by primer walking over the insert using the degenerate amplification primers (Seq. ID Nos. 1 and 2) as initial extension primers. Then, subsequent extension primers were constructed by looking at the previously-generated sequence data. The sequence of the xylanase gene and putative amino acid sequence of the encoded-xylanase are set forth herein as Seq. ID No. 24.

We claim:

1. A method for recovering xylanase-encoding DNA from soil, comprising the steps of:
   (a) treating a soil sample to render DNA in the soil accessible for hybridization with oligonucleotide primers,
   (b) combining the treated soil sample with first and second amplification primers in an amplification reaction mixture, said first and second amplification primers hybridizing with conserved regions of the sense and antisense strands respectively of a gene encoding a xylanase and flanking a region of interest in the gene,
   (c) thermally cycling the amplification reaction mixture through a plurality of cycles each including at least a denaturation phase and a primer extension phase to produce multiple copies of the region of interest flanked by the first and second amplification primers, and
   (d) recovering the copies of the region of interest from the amplification reaction mixture, wherein the method further comprises the step of screening a treated soil sample to isolate full length DNA encoding a complete xylanase using a probe having a sequence which is the same as or fully complementary to at least a portion of a recovered copy of the region of interest, said portion being different from the reference xylanase sequence given by SEQ ID NO 23.

2. The method according to claim 1, wherein the probe has a sequence which is the same as or fully complementary to at least a portion of any one of Seq. ID Nos. 3 through 22 that is different from the reference xylanase sequence given by Seq. ID. No. 23.

3. The method according to claim 1, wherein the probe has a sequence which is the same as or fully complementary to any one of Seq. ID Nos. 3 through 22.

4. A method for recovering a xylanase gene from soil, comprising the steps of:
   (a) combining a treated soil sample in which soil DNA is rendered accessible for hybridization with a polynucleotide probe having a sequence which is the same as or fully complementary to at least a portion of any one of Seq. ID Nos. 3 through 22 that is different from the reference xylanase sequence given by Seq. ID. No. 23; and
   (b) isolating DNA that hybridizes with the probe from the treated soil sample, thereby recovering a xylanase gene from the soil sample.

5. The method according to claim 4, wherein the treated soil sample is a phage library prepared from a soil sample.

6. A polynucleotide probe for isolation or identification of xylanase genes having a sequence which is the same as or fully complementary to at least a portion of any one of Seq. ID Nos. 3 through 22 that is different from the reference xylanase sequence given by Seq. ID. No. 23.

7. A polynucleotide probe for isolation or identification of xylanase genes having a sequence which is the same as or fully complementary to any one of Seq. ID Nos. 3 through 22.

* * * * *